(12) United States Patent
Matsuno et al.

(10) Patent No.: US 10,248,227 B2
(45) Date of Patent: Apr. 2, 2019

(54) WEARABLE TERMINAL DEVICE AND IMAGE PROCESSING METHOD

(71) Applicant: Seiko Epson Corporation, Tokyo (JP)

(72) Inventors: Atsuhiko Matsuno, Azumino (JP); Yoshihiro Tatara, Shiojiri (JP); Yosuke Wakamiya, Matumoto (JP); Tomohiro Ogawa, Shiojiri (JP); Susumu Honda, Kyoto (JP)

(73) Assignee: Seiko Epson Corporation, Tokyo (JP)

( * ) Notice: Subject to any disclaimer, the term of this patent is extended or adjusted under 35 U.S.C. 154(b) by 111 days.

(21) Appl. No.: 15/291,981

(22) Filed: Oct. 12, 2016

(65) Prior Publication Data

US 2017/0115752 A1     Apr. 27, 2017

(30) Foreign Application Priority Data

Oct. 26, 2015   (JP) ................................ 2015-209540

(51) Int. Cl.
*A61B 5/00* (2006.01)
*A61B 5/11* (2006.01)
(Continued)

(52) U.S. Cl.
CPC ........... *G06F 3/0362* (2013.01); *G01C 17/28* (2013.01); *G01C 22/006* (2013.01); *G04B 47/06* (2013.01);
(Continued)

(58) Field of Classification Search
CPC .... G06F 3/0416; G06F 1/163; G06F 3/04886; G06F 3/04817; G06F 2203/04803;
(Continued)

(56) References Cited

U.S. PATENT DOCUMENTS

2009/0059730 A1*   3/2009   Lyons ................... G04G 21/08
                                                                368/69
2011/0099512 A1*   4/2011   Jeong ................... G06F 3/0481
                                                                715/790

(Continued)

FOREIGN PATENT DOCUMENTS

JP           61-72697 U      5/1986
JP        2002-174688 A      6/2002

*Primary Examiner* — Haixia Du
(74) *Attorney, Agent, or Firm* — ALG Intellectual Property, LLC

(57) ABSTRACT

A wearable terminal device includes a display section configured to display a display image and a processing section. The processing section performs processing for displaying any one kind of information among information of a first information type to information of an N-th information type in respective display regions of first to M-th display regions obtained by dividing the display image, when the display image is switched from a first display image to a second display image, changes the size of at least an i-th display region among the first to M-th display regions, in the first display image, performs processing for displaying information of a j-th information type in the i-th display region at a first information verbosity, and, in the second display image, performs processing for displaying the information of the j-th information type in the i-th display region, the size of which is changed, at a second information verbosity different from the first information verbosity.

17 Claims, 17 Drawing Sheets

(51) Int. Cl.
  *G06F 1/16* (2006.01)
  *G06F 3/01* (2006.01)
  *G01C 17/28* (2006.01)
  *G01C 22/00* (2006.01)
  *G04B 47/06* (2006.01)
  *G06F 3/0362* (2013.01)
  *G06F 3/0484* (2013.01)
  *G06F 3/0487* (2013.01)

(52) U.S. Cl.
  CPC .............. *G06F 1/163* (2013.01); *G06F 3/011* (2013.01); *G06F 3/014* (2013.01); *G06F 3/0484* (2013.01); *G06F 3/0487* (2013.01); *A61B 5/1118* (2013.01); *A61B 5/681* (2013.01); *A61B 5/743* (2013.01); *G06F 2203/04803* (2013.01)

(58) Field of Classification Search
  CPC ...... G06F 2200/1637; G09G 2340/145; G09G 2354/00; G09G 2320/08; G09G 2340/14; G04G 21/08; A61B 5/681; A61B 5/02438; A61B 5/6802; A61B 5/6824; H04N 21/4314; H04N 21/4312
  See application file for complete search history.

(56) References Cited

U.S. PATENT DOCUMENTS

| | | | |
|---|---|---|---|
| 2015/0067366 A1* | 3/2015 | Lai ........................ | G06F 1/3293 713/320 |
| 2015/0363065 A1* | 12/2015 | Kim ...................... | G06F 3/0482 715/739 |
| 2016/0170579 A1* | 6/2016 | Li ......................... | G06F 3/0482 715/778 |
| 2016/0239142 A1* | 8/2016 | Kim ...................... | G06F 3/0416 |

* cited by examiner

| INFORMATION TYPE | | DAILY LIFE | EXERCISE |
|---|---|---|---|
| BIOLOGICAL DETECTION INFORMATION | PULSE RATE | — | ○ |
| | BLOOD PRESSURE | — | ○ |
| ACTIVITY DETECTION INFORMATION | NUMBER OF STEPS | — | ○ |
| | MOVING DISTANCE | — | ○ |
| DATE AND TIME INFORMATION | DATE (CALENDAR) | ○ | — |
| | TIME (WATCH) | ○ | — |
| | ALARM SETTING | ○ | — |
| ENVIRONMENT DETECTION INFORMATION | TEMPERATURE | — | ○ |
| | ALTITUDE | — | ○ |
| | ATMOSPHERIC PRESSURE | — | ○ |
| | AZIMUTH | — | ○ |
| OTHERS | STOPWATCH | — | ○ |
| | MUSIC PLAYER | ○ | ○ |

FIG. 9

WEARABLE TERMINAL DEVICE AND IMAGE PROCESSING METHOD

CROSS-REFERENCES TO RELATED APPLICATIONS

This application claims priority to Japanese Patent Application No. 2015-209540, filed Oct. 26, 2015, the entirety of which is herein incorporated by reference.

BACKGROUND

1. Technical Field

The present invention relates to a wearable terminal device, an image processing method, and the like.

2. Related Art

In recent years, wearable terminal devices (electronic devices) such as a wristwatch-type terminal device have become multifunctional. Information concerning a plurality of functions needs to be properly displayed. As a wearable terminal device that displays information concerning a plurality of functions, for example, a wristwatch-type terminal device including a plurality of memory scales (dial scales) provided for respective functions is publicly known.

JP-UM-A-61-072697 (Patent Literature 1) discloses, as the wearable terminal device that displays information concerning a plurality of functions, a rotary bezel-attached electronic watch including a rotary bezel. In the rotary bezel-attached electronic watch disclosed in Patent Literature 1, as shown in FIG. 2 of the literature, when the rotary bezel is rotated, the position of a frame body dividing a display section changes, a mode changes, and information displayed on the display section changes.

JP-A-2002-174688 (Patent Literature 2) discloses an electronic wristwatch including a rotary bezel. In the electronic wristwatch disclosed in Patent Literature 2, when the rotary bezel is rotated, the positions of a plurality of provided display window sections change, whereby a mode changes.

A wearable terminal device provided with a plurality of memory scales on a display surface (a dial) has a problem in easiness of reading of information. For example, when a plurality of memory scales are present under hands, it is hard to distinguish which memory scale a value indicated by the hands corresponds. Moreover, it is difficult to determine display content only with a numerical value.

Functions implemented in the wearable terminal device are various functions including not only time display but also, for example, display of a pulse, altitude, temperature, the number of steps, and play and stop of music. However, when a plurality of kinds of information are simultaneously displayed on a display section of the wearable terminal device, a display space that can be allocated to the respective kinds of information is limited. It is difficult to display necessary information in detail.

On the other hand, actually, information that should be displayed in one screen is limited to each user. That is, there is little necessity to display, in the screen, even details of information concerning function not used by the user. It is undesirable in terms of efficiency of use of the display screen to display even the details of the information concerning the functions not in use.

SUMMARY

An advantage of some aspects of the invention is to provide a wearable terminal device, an image processing method, and the like that can display, in such a manner as to be easily distinguished and in detail, a plurality of kinds of information in one screen and display information that a user desired to know.

An aspect of the invention relates to a wearable terminal device including: a display section configured to display a display image; and a processing section configured to perform display control of the display image in the display section. The processing section performs processing for displaying any one kind of information among information of a first information type to information of an N-th information type (N is an integer equal to or larger than 2) in respective display regions of a first display region to an M-th display region (M is an integer equal to or larger than 2) obtained by dividing the display image, when the display image is switched from a first display image to a second display image, changes the size of at least an i-th display region (i is an integer equal to or larger than 1 and equal to or smaller than M) among the first display region to the M-th display region, in the first display image, performs processing for displaying information of a j-th information type (j is an integer equal to or larger than 1 and equal to or smaller than N) in the i-th display region at a first information verbosity, and, in the second display image, performs processing for displaying the information of the j-th information type in the i-th display region, the size of which is changed, at a second information verbosity different from the first information verbosity.

In the aspect of the invention, the processing section performs processing for displaying a plurality of kinds of information having different information types in a plurality of display regions obtained by dividing the display image. When the display image is switched from the first display image to the second display image, the processing section changes the size of at least the i-th display region among the first display region to the M-th display region. Further, the processing section performs processing for displaying, in the i-th display region of the second display image, information having an information type same as an information type of information displayed in the i-th display region in the first display image and having an information verbosity different from an information verbosity of the information displayed in the i-th display region in the first display image. Therefore, it is possible to display a plurality of kinds of information in one screen and display, in such a manner as to be easily distinguished and in detail, information that a user desires to know.

In the aspect of the invention, when the display image is switched from the first display image to the second display image, the processing section may increase the size of at least the i-th display region and, in the second display image, perform processing for displaying the information of the j-th information type in the enlarged i-th display region at the second information verbosity higher than the first information verbosity.

With this configuration, it is possible to, while displaying a plurality of kinds of information in one screen, display, in the enlarged display region, in such a manner as to be easily distinguished and in detail, information that the user desires to known.

In the aspect of the invention, when the display image is switched from the first display image to the second display image, the processing section may reduce the size of at least the i-th display region and, in the second display image, perform processing for displaying the information of the j-th information type in the reduced i-th display region at the second information verbosity lower than the first information verbosity.

With this configuration, it is possible to, for example, display, at a necessary minimum information verbosity, information other than information that the user desires to know in detail.

In the aspect of the invention, the information of the first information type to the information of the N-th information type may include at least one of biological detection information and activity detection information and at least one of time information and environment detection information.

With this configuration, it is possible to, for example, simultaneously display at last two kinds of information on the display section.

In the aspect of the invention, the wearable terminal device may further include a detecting section configured to detect operation of an operation section, and the processing section may perform processing for, when given operation on the operation section is detected by the detecting section, switching the display image from the first display image to the second display image and displaying the display image.

With this configuration, it is possible to, for example, switch the display image from the first display image to the second display image according to the intention of the user.

In the aspect of the invention, the operation section may be a member rotatable around a given rotation axis, and the processing section may perform processing for, when rotating operation of the operation section serving as the given operation is detected by the detecting section, switching the display image from the first display image to the second display image and displaying the display image.

With this configuration, when the user performs simple operation for rotating a rotary bezel or a crown, it is possible to, for example, switch the display image from the first display image to the second display image.

In the aspect of the invention, the processing section may increase or reduce the size of the i-th display region in a direction corresponding to a rotating direction of the rotating operation.

With this configuration, the user determines the rotating direction for rotating the operation section, whereby it is possible to, for example, enlarge any display region.

In the aspect of the invention, the processing section may perform processing for, when the display image is switched from the first display image to the second display image and the i-th display region is enlarged, displaying a guide object of a command in a position corresponding to a position of the operation section and, when the given operation on the operation section is detected by the detecting section, execute the command corresponding to the guide object.

With this configuration, it is possible to, for example, smoothly guide operation by the user to a function corresponding to information displayed in the enlarged display region. By displaying the guide object, it is possible to, for example, explain and indicate functions of the wearable terminal device to the user.

In the aspect of the invention, the processing section may perform switching processing of a daily life mode and an exercise mode and perform processing for, when the wearable terminal device is set in the daily life mode, displaying P kinds of information (P is an integer equal to or larger than 1 and equal to or smaller than N) of an information type associated with the daily life mode among the information of the first information type to the information of the N-th information type and, when the wearable terminal device is set in the exercise mode, displaying Q pieces of information (Q is an integer equal to or larger than 1 and equal to or smaller than N) of an information type associated with the exercise mode among the information of the first information type to the information of the N-th information type.

With this configuration, it is possible to, for example, display, in the daily life mode, information that the user frequently view in a daily life and display, in the exercise mode, information that the user views during exercise.

In the aspect of the invention, the number of objects for transmitting information may be larger for information, the information verbosity of which is high, than information, the information verbosity of which is low.

With this configuration, when information is displayed in detail, it is possible to, for example, display a large number of objects and inform the user of a lot of information.

In the aspect of the invention, information, the information verbosity of which is low, may be an icon, and information, the information verbosity of which is high, may be the icon and numerical value information.

With this configuration, it is possible to, for example, by displaying the icon, make it easy to instantaneously grasp information while reducing a display region and, when detailed display is performed, display accurate and detailed information according to the numerical value information.

In the aspect of the invention, the respective display regions of the first display region to the M-th display region may be divided into pie shapes or may be formed in concentric circle shapes.

With this configuration, it is possible to, for example, efficiently make use of a display space and display information that is more clearly understood when being disposed in a circular shape.

Another aspect of the invention relates to a wearable terminal device including: a display section configured to display a display image; and a processing section configured to perform display control of the display image in the display section. The processing section performs processing for displaying biological detection information or activity detection information in a first display region among the first display region to an M-th display region (M is an integer equal to or larger than 2) obtained by dividing the display image into pie shapes or concentric circle shapes and displaying time information or environment detection information in a second display region among the first display region to the M-th display region.

Still another aspect of the invention relates to a wearable terminal device including: a display section including a first display region for displaying first information and a second display region for displaying second information; a processing section configured to perform display control of the display section; and an operation section that is in an electric communication relation with the processing section. The processing section performs display processing for, on the basis of a signal from the operation section, setting the first display region larger than the second display region and increasing an information verbosity concerning the first display image displayed in the first display region.

With these configurations, it is possible to, for example, while displaying a plurality of kinds of information in one screen, display, in the enlarged display region, in such a manner as to be easily distinguished and in detail, information that the user desires to know.

In the another aspect of the invention, the processing section may perform, as the display processing for increasing the information verbosity, at least any one kind of processing among processing for increasing display items of information concerning the first information, processing for displaying a time series change of the first information, processing for increasing temporal resolution of the time series change of the first information, and processing for displaying derived information derived on the basis of the first information.

With this configuration, it is possible to, for example, increase the display items, display the time series change, display the time series change more in detail, and display the information that can be derived from the first information to increase the information verbosity of the first information.

In the another aspect of the invention, the first information may be information concerning any one of a pulse rate, the number of steps, an azimuth, time of day, date and time, an activity amount, a calorie balance, and a sleeping time.

With this configuration, it is possible to, for example, display, in the first display region, the information concerning any one of the pulse rate, the number of steps, the azimuth, the time of day, the date and time, the activity amount, the calorie balance, and the sleeping time while changing the information verbosity as appropriate.

Yet another aspect of the invention relates to an image processing method including: performing processing for displaying any one kind of information among information of a first information type to information of an N-th information type (N is an integer equal to or larger than 2) in respective display regions of a first display region to an M-th display region (M is an integer equal to or larger than 2) obtained by dividing a display image; increasing, when the display image is switched from a first display image to a second display image, the size of at least an i-th display region (i is an integer equal to or larger than 1 and equal to or smaller than M) among the first display region to the M-th display region; performing, in the first display image, processing for displaying information of a j-th information type (j is an integer equal to or larger than 1 and equal to or smaller than N) in the i-th display region at a first information verbosity; and, performing, in the second display image, processing for displaying the information of the j-th information type in the enlarged i-th display region, at a second information verbosity different from the first information verbosity.

BRIEF DESCRIPTION OF THE DRAWINGS

The invention will be described with reference to the accompanying drawings, wherein like numbers reference like elements.

FIG. 9 is an explanatory diagram of information types.

DESCRIPTION OF EXEMPLARY EMBODIMENTS

An embodiment is explained below. Note that the embodiment explained below does not unduly limit the content of the invention described in the appended claims. Not all of components explained in the embodiment are essential constituent elements of the invention.

1. Overview

A wearable terminal device in this embodiment is capable of displaying information of a plurality of information types and displays, in such a manner as to be easily distinguished and in detail, information that a user desires to know. Examples of the wearable terminal device include a wristwatch-type terminal device shown in FIG. 2 referred to below.

Figure 5:
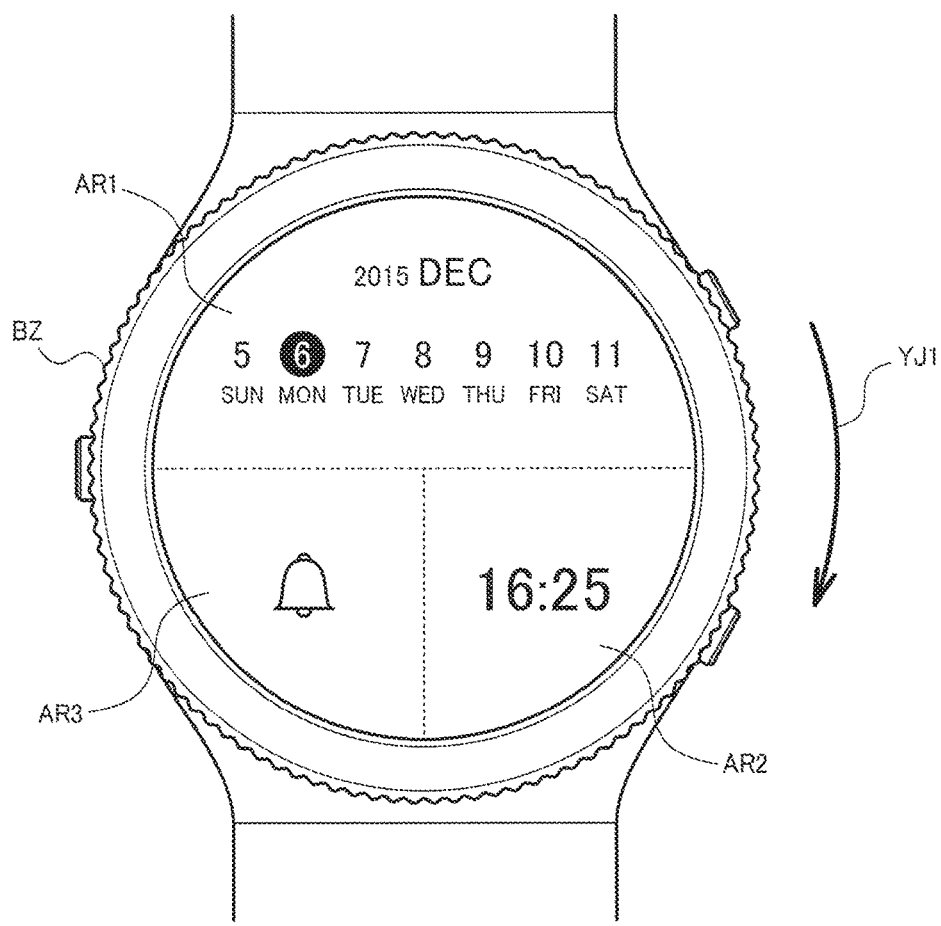
FIG. 5 is an explanatory diagram of a display image displayed in a daily life mode.
Figure 6:
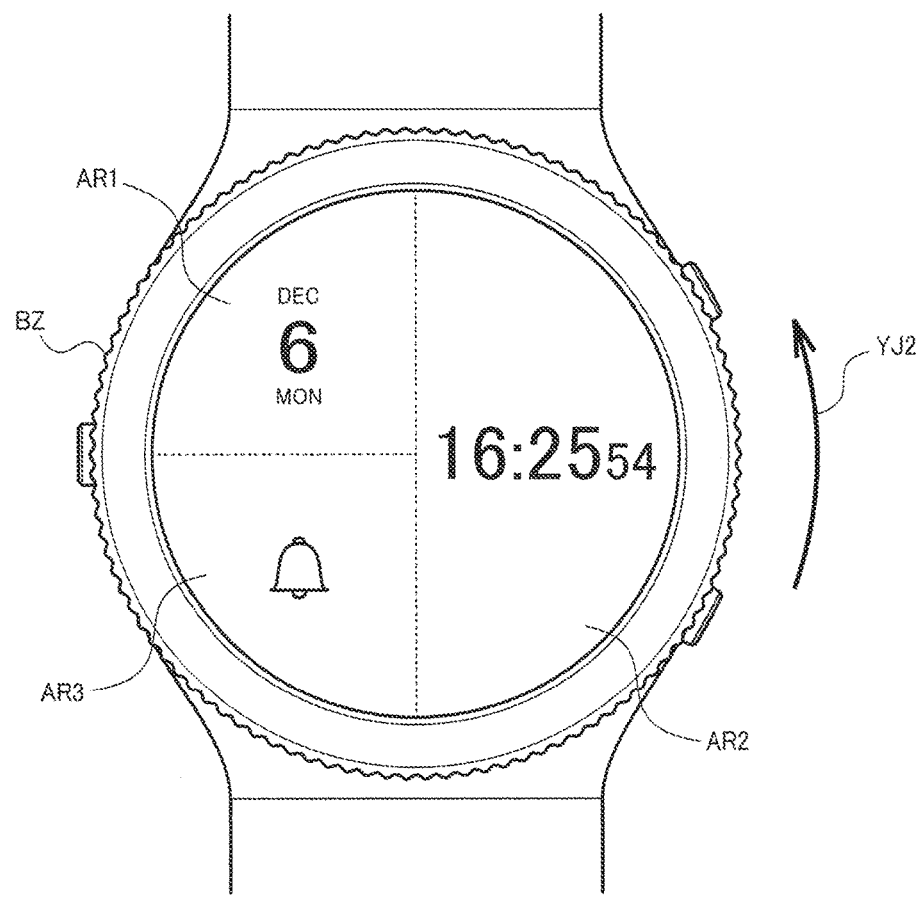
FIG. 6 is an explanatory diagram of another display image displayed in the daily life mode.

The wristwatch-type terminal device in this embodiment includes, as shown in FIG. 5 referred to below, a display panel (a display section) on which a display image is displayed and a rotary bezel BZ. The display image is divided in a plurality of display regions (AR1 to AR3) of pie shapes. For example, as shown in FIG. 6 referred to below, when a user (an wearer) of the wristwatch-type terminal device rotates the rotary bezel BZ in a direction indicated by an arrow YJ2, the positions and the sizes of the display regions change in association with the rotation. For example, in an example shown in FIG. 6, the display region AR2 is enlarged from a state shown in FIG. 5. A region in the right half of the display image is the display region AR2. On the other hand, the display region AR1 shown in FIG. 6 is reduced from a state shown in FIG. 5. Only an upper left region of the display region is the display region AR1.

More information can be displayed in the enlarged display region by an enlarged area of the region. If only information of a single information type is displayed in the display regions, it is not hard to view the information. Therefore, the wristwatch-type terminal device in this embodiment displays more detailed information in a display region, the size of which is increased, and displays simple information such as an icon in a display region, the size of which is reduced.

For example, when the user desires to know time of day in detail, the user only has to rotate the rotary bezel BZ as shown in FIG. 6 and cause the wristwatch-type terminal device to display time information in detail. When the user desires to view a calendar in detail, the user only has to rotate the rotary bezel BZ to change the wristwatch-type terminal device to a state shown in FIG. 5. In this way, by rotating the rotary bezel BZ, the user can select information to be displayed in detail.

Therefore, the wearable terminal device in this embodiment can display information of a plurality of information types and display, in such a manner as to be easily distinguished and in detail, information that the user desires to know.

2. Sycrown Configuration Example

Figure 1:
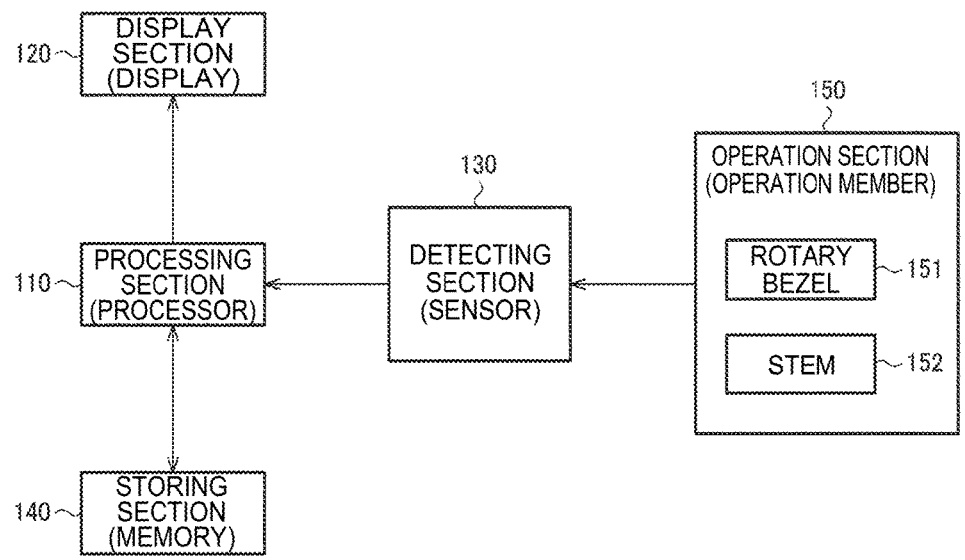
FIG. 1 is an explanatory diagram of a sycrown configuration example in an embodiment.

A configuration example of a wearable terminal device (a wristwatch-type terminal device, an electronic device) 100 in this embodiment is shown in FIG. 1. The wearable terminal device 100 in this embodiment includes a processing section 110 and a display section 120. The wearable terminal device 100 may include, as shown in FIG. 1, a detecting section 130, a storing section 140, and an operation member (an operation section) 150. The operation member 150 includes, for example, a rotary bezel 151 and a crown 152. Note that the wearable terminal device 100 is not limited to the configuration shown in FIG. 1. Various modified implementations for omitting a part of the components and adding other components are possible.

Figure 2:
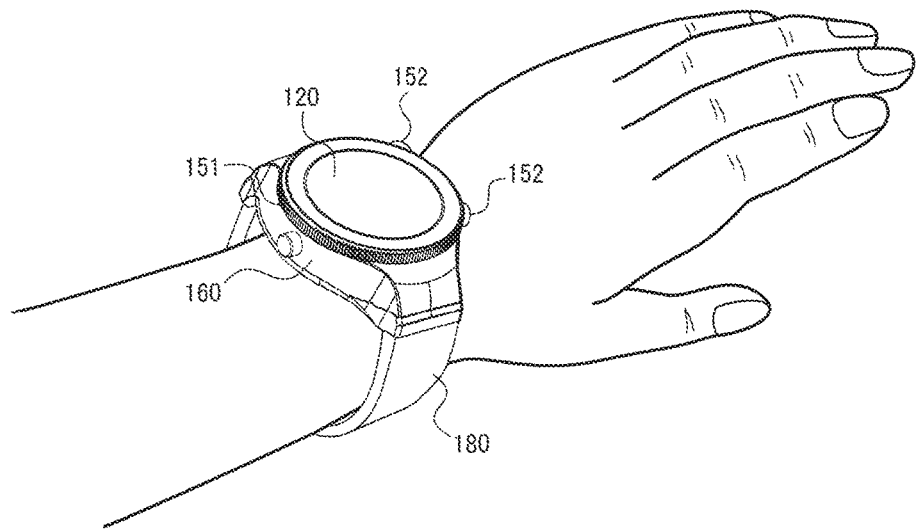
FIG. 2 is an explanatory diagram of a specific configuration example of a wristwatch-type terminal device.

As shown in FIG. 2, for example, when the wearable terminal device 100 is a wristwatch-type terminal device, the wearable terminal device 100 includes a housing 160 and a band section 180 attached to the housing 160. The housing 160 is a member equivalent to a main body section of the wearable terminal device 100. Operation members such as the rotary bezel 151 and the crown 152 and the display section 120 are provided in the housing 160. The housing 160 may incorporate the processing section 110, the storing section 140, and the like. The housing 160 may include, on the inside, for example, a board (a circuit board) on which the processing section 110 is mounted. As shown in FIG. 2, the band section 180 is wound on a wrist or the like of the user (the wearer) to fix the wearable terminal device 100.

Processing performed by the sections of the wearable terminal device 100 is explained.

The display section 120 (a display) is a section for performing various kinds of display such as display of a display image. The display section 120 can be realized by, for example, a liquid crystal display or an organic EL display.

The processing section 110 performs display control of a display image in the display section 120. The processing section 110 may be a processor realized by various components such as a hardware circuit by a CPU (Central Processing Unit), a GPU (Graphics Processing Unit), a DSP (Digital Signal Processor), or an ASIC (application specific integrated circuit).

The storing section 140 functions as a work area of the processing section 110 and the like. A function of the storing section 140 can be realized by a memory such as a RAM, a HDD (hard disk drive), or the like. A specific example of information stored in the storing section 140 is explained below with reference to FIG. 4 and the like.

The operation member 150 is, for example, a member rotatable around a given rotation axis. For example, as explained above, the operation member 150 includes the rotary bezel 151 and the crown 152. However, the operation member 150 is not limited to these members and may be, for example, a button or a switch.

The rotary bezel 151 is a member equivalent to a frame of the housing 160 (in a narrow sense, the display section 120). The rotary bezel 151 is provided in a position equivalent to the circumferential edge portion of the housing 160, in particular, the outer circumference of the display section 120. In particular, the rotary bezel 151 according to this embodiment is a rotary bezel rotatable around a given axis set as a rotation axis. The given axis is, for example, an axis in a direction crossing the display section 120 and, in a narrow sense, an axis in a direction orthogonal to the display section 120. However, in a method in this embodiment, another rotation member may be used instead of the rotary bezel.

The crown (a crown) 152 is, as shown in FIG. 2, for example, a protrusion section provided on a side surface section of the housing 160. The crown 152 is rotatable around a given axis set as a rotation axis. The given axis is, for example, an axis in a direction crossing the side surface section of the housing 160 and, in a narrow sense, an axis in a direction orthogonal to the side surface section of the housing 160. The position of the crown 152 may be able to be changed with respect to the side surface section of the housing 160 by, for example, being pushed and pulled. However, in the method in this embodiment, another member such as a button or a switch may be used instead of the crown 152.

The detecting section 130 detects operation performed using the operation member 150. For example, when the operation member 150 includes the rotary bezel 151, the wearable terminal device 100 may include a not-shown number-of-pulses detection sensor as the detecting section 130. A given optical pattern is provided on the lower surface of the rotary bezel 151. The number-of-pulses detection sensor radiates light on the lower surface of the rotary bezel 151 and detects reflected light of the light. In this way, the number of pulses detected by the number-of-pulses detection sensor has a correlation with a rotation amount of the rotary bezel 151. Therefore, it is possible to detect a rotation state (in a narrow sense, a rotating direction and a rotation amount) of the rotary bezel 151 on the basis of sensor information. However, a detecting method for the rotation state of the rotary bezel in this embodiment is not limited to this. Other widely-known methods of detecting the rotation state of the rotary bezel (e.g., a method of detecting the rotation state of the rotary bezel with a mechanical structure) can be widely applied. Therefore, the detecting section 130 in this embodiment can be realized by various sensors and the like used in various methods.

3. Details of Processing

Details of processing in this embodiment are explained.

The processing section 110 performs processing for displaying a plurality of kinds of information having different information types in a plurality of display regions obtained by dividing a display image. In other words, the processing section 110 performs processing for displaying, on the display section 120, any one kind of information among information of a first information type to information of an N-th information type (N is an integer equal to or larger than 2) in respective display regions of a first display region to an M-th display region (M is an integer equal to or larger than 2) obtained by dividing a display image. Respective kinds of processing in this embodiment performed by the processing section 110 (a processor) is executed on the basis of information (various data or computer programs) stored in the storing section 140 (a memory).

Figure 3:
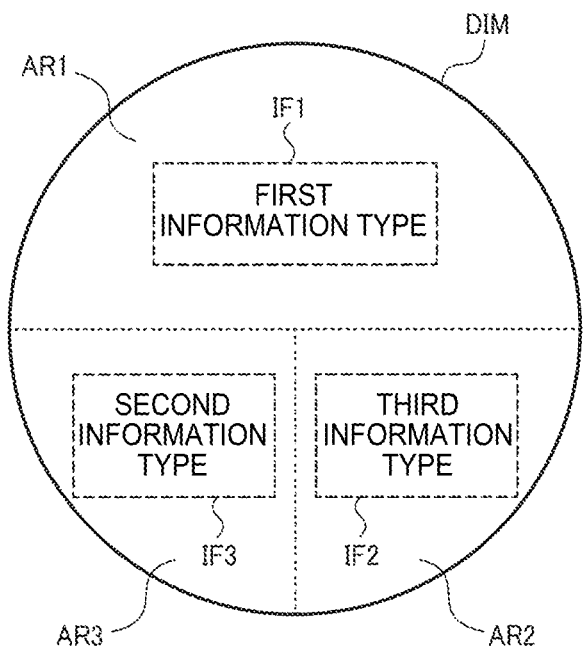
FIG. 3 is an explanatory diagram of a display image and a plurality of display regions.

The display image includes, for example, M display regions as shown in FIG. 3. In an example shown in FIG. 3, M is 3. A display image DIM includes three display regions (AR1 to AR3). For example, in the example shown in FIG. 3, information IF1 of the first information type is displayed in the first display region AR1, information IF2 of the second information type is displayed the second display region AR2, and information IF3 of the third information type is displayed in the third display region AR3. The information types displayed in the display regions can be optionally combined. For example, although not shown in the figure, when N is 5, information IF4 of a fourth information type may be displayed in the first display region AR1, information IF5 of a fifth information type may be displayed in the second display region AR2, and the information IF1 of the first information type may be displayed in the third display region AR3. Other combinations are also possible. In this case, information types not displayed in all the display regions may be present. For example, in the example in which N is 5, the information IF2 of the second information type and the information IF3 of the third information type are not displayed in all the display regions. Note that, in the example shown in FIG. 3, the kinds of information of the information types different from one another are displayed in the respective display regions. However, this embodiment is not limited to the display. In a certain display region, information of an information type same as an information type displayed in another display region may be displayed.

When the display image is switched from a first display image to a second display image, the processing section 110 changes the size of at least an i-th display region (i is an integer equal to or larger than 1 and equal to or smaller than M) among the first display region to the M-th display region.

Figure 4:
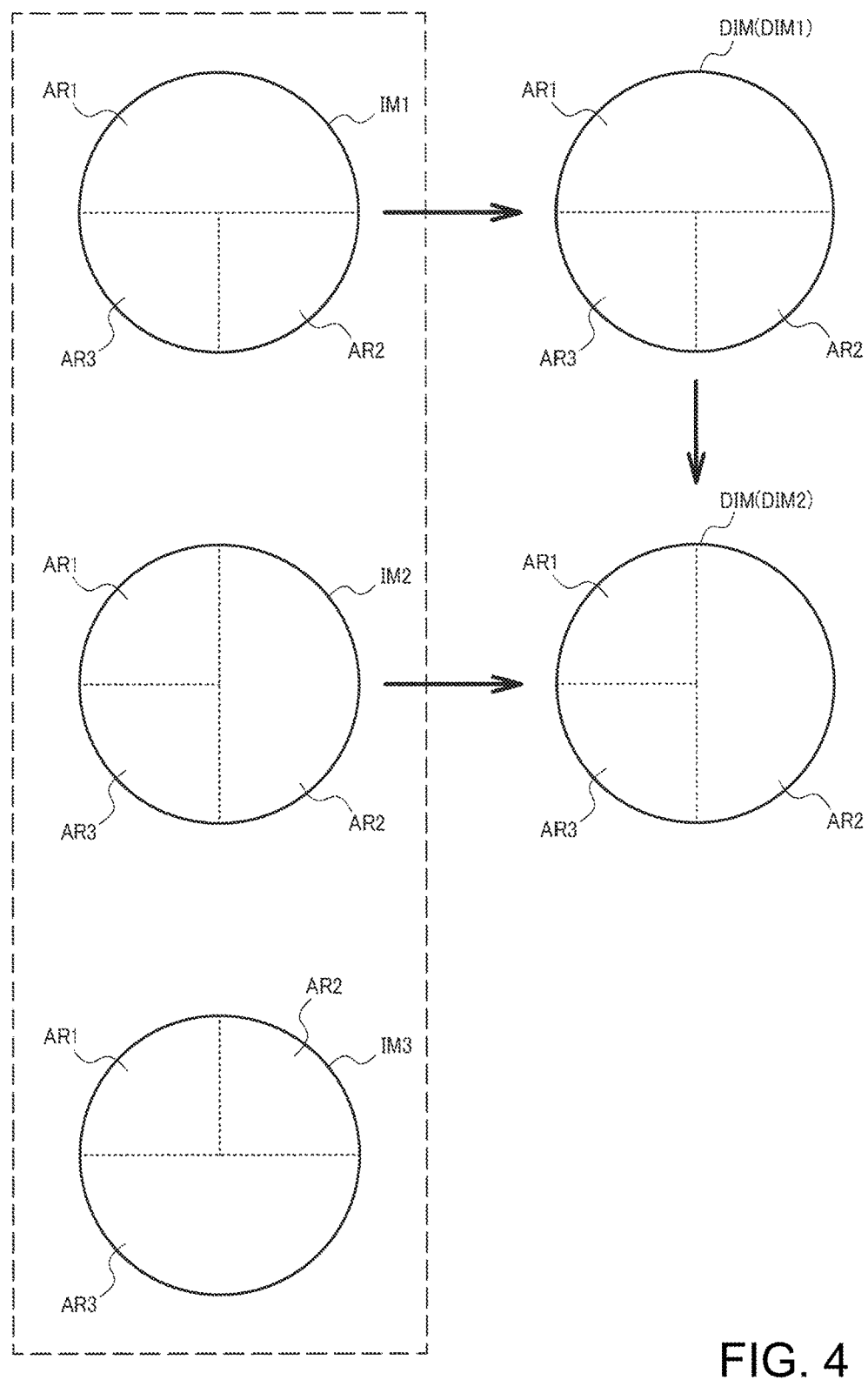
FIG. 4 is an explanatory diagram of switching processing for the display image.

A plurality of images are stored in the storing section 140. For example, in an example shown in FIG. 4, three images (IM1 to IM3) are stored in the storing section 140. The processing section 110 selects (specifies) an image IM1 out of three images (IM1 to IM3) as the display image DIM (a first display image DIM1). As shown in FIG. 4, each of the plurality of images (IM1 to IM3) stored in the storing section 140 includes three display regions (AR1 to AR3) (M=3). Divisions (shapes) for the display regions are different among the plurality of images. For example, in the image IM1, the display region AR1 is a widest display region. However, in the image IM2, the display region AR2 is a widest display region and, in the image IM3, the display region AR3 is a widest display region. Note that the plurality of images stored in the storing section 140 may be an image group stored in the storing section 140 in advance or may be an image group generated by the processing section 110.

In the example shown in FIG. 4, if the processing section 110 selects (specifies) the image IM2 as the display image DIM next, it is possible to change the sizes of the display region AR1 and the display region AR2 of the display image DIM (i=1 or 2). In this case, the image IM1 is the first display image DIM1 and the image IM2 is a second display image DIM2. Note that the first display image is a display image displayed on the display section 120 before the change of the display image. The second display image is a display image displayed on the display section 120 after the change of the display image.

Further, although not shown in FIG. 4, if the processing section 110 selects (specifies) the image IM3 as the display image DIM in a state in which the image IM2 is the display image DIM, it is possible to change the sizes of the display region AR2 and the display region AR3 of the display image DIM (i=2 or 3). In this case, the image IM2 is the first display image and the image IM3 is the second display image.

The processing section 110 performs processing for displaying, in the i-th display region of the second display image, information having an information type same as an information type of the information displayed in the i-th display region in the first display image and having an information verbosity different from an information verbosity of the information displayed in the i-th display region in the first display image. That is, the processing section 110 performs, in the first display image, processing for displaying information of a j-th information type (j is an integer equal to or larger than 1 and equal to or smaller than N) in the i-th display region at a first information verbosity, and, in the second display image, performs processing for displaying the information of the j-th information type in the i-th display region, the size of which is changed, at a second information verbosity different from the first information verbosity.

A specific example is explained with reference to FIGS. 5 and 6. First, in the example shown in FIGS. 5 and 6, a display image including three display regions (AR1 to AR3) is displayed on the display section. Divisions of display regions are different in the display image shown in FIG. 5 and the display image shown in FIG. 6. In both the display images, calendar information is displayed in the first display region AR1, time information is displayed in the second display region AR2, and alarm setting information is displayed in the third display region AR3. When the explanation of FIG. 3 and a state shown in FIG. 5 are collated, the first information type is a calendar, the second information type is time of day, and the third information type is alarm setting.

The display image shown in FIG. 5 is set as the first display image, the display image shown in FIG. 6 is set as the second display image, and the display image is switched from the display image shown in FIG. 5 to the display image shown in FIG. 6. At this point, in the display image shown in FIG. 5, calendar information for one week is displayed in the widest display region AR1. In the display image shown in FIG. 6, calendar information for one day is displayed in the display region AR1, the size of which is changed. In the calendar information displayed in the display region AR1 of the display image shown in FIG. 5 and the calendar information displayed in the display region AR1 of the display image shown in FIG. 6, information types are the same but information verbosities are different. If this is applied to the above explanation, the i-th display region is the display region AR1 (i=1) and the j-th information type is the calendar. The calendar information displayed in the display region AR1 shown in FIG. 5 is more detailed than the calendar information displayed in the display region AR1 shown in FIG. 6. The first information verbosity is higher than the second information verbosity.

On the other hand, in the display image shown in FIG. 5, the time information is displayed in minute units in the display region AR2. In the display image shown in FIG. 6, the time information is displayed in second units in the widest display region AR2, the size of which is changed. At this point, in the time information displayed in the display region AR2 of the display image shown in FIG. 5 and the time information displayed in the display region AR2 of the display image shown in FIG. 6, information types are the same but information verbosities are different. If this is applied to the above explanation, the i-th display region is the display region AR2 (i=2) and the j-th information type is the time of day. The time information displayed in the display region AR2 shown in FIG. 6 is more detailed than the time information displayed in the display region AR2 shown in FIG. 5. The second information verbosity is higher than the first information verbosity.

That is, as shown in FIGS. 5 and 6, when the user desires to know calendar information for one week in detail, the user only has to cause the wearable terminal device 100 to display the first display image shown in FIG. 5. When the user desires to know the time information in detail to second units, the user only has to cause the wearable terminal device 100 to display the second display image shown in FIG. 6. As in this example, if detailed information is displayed in a widest display region, it is possible to sufficiently secure a display space in which information of a certain information type is displayed with a large information amount. It is possible to make it easier to distinguish information that the user desires to know. By displaying simple information in another display region, the user can simultaneously check another kind of information while checking details of certain information. Further, as explained above, since the display regions are divided for the respective information types, even if a plurality of kinds of information are displayed in one display image, it does not occur that information is disordered and hard to be distinguished.

Therefore, it is possible to display a plurality of kinds of information in one screen and display, in such a manner as to be easily distinguished and in detail, information that the user desires to know.

As shown in FIGS. 5 and 6, when the display image is switched from the first display image to the second display image, there are a display region, the size of which increases, like AR2 and a display region, the size of which decreases, like AR1. In the following explanation, the enlargement of the display region and the reduction of the display region are separately explained.

First, information that the user desires to know needs to be displayed in such a manner as to be easily distinguished and in detail. However, information having a high verbosity has a large information amount. A wide display region is necessary to display the information. When the wide display region cannot be secured, a display size of the information has to be reduced. However, it is not advisable to reduce the display size of the information because it is hard for the user to distinguish the information.

Therefore, in this embodiment, the size of a display region where information that the user desires to know is displayed is increased. Specifically, when the display image is switched from the first display image to the second display image, the processing section 110 increases the size of at least the i-th display region. The processing section 110 performs processing for displaying, in the i-th display region of the second image, information having an information type same as the information type of the information displayed in the i-th display region in the first display image and having an information verbosity higher than and the information verbosity of the information displayed in the i-th display region in the first display image. That is, the processing section 110 performs, in the first display image, processing for displaying the information of the j-th information type in the i-th display region at the first information verbosity and, in the second display image, processing for displaying the information of the j-th information type in the enlarged i-th display region at the second information verbosity higher than the first information verbosity.

In other words, the wearable terminal device 100 in this embodiment includes the display section 120 including the first region where the first information is displayed and the second display region where the second information is displayed, the processing section 110 that performs display control of the display section 120, and the operation section 150 that is in an electric communication relation with the processing section 110. The processing section 110 performs, on the basis of a signal from the operation section 150, display processing for setting the first display region larger than the second display region and increasing an information verbosity concerning the first information displayed in the first display region.

For example, as explained above, in the first display image shown in FIG. 5, the time information is displayed in the display region AR2 in minute units. However, in the second display image shown in FIG. 6, the time information is displayed in the display region AR2, the size of which is increased, in detail to second units.

Figure 7:
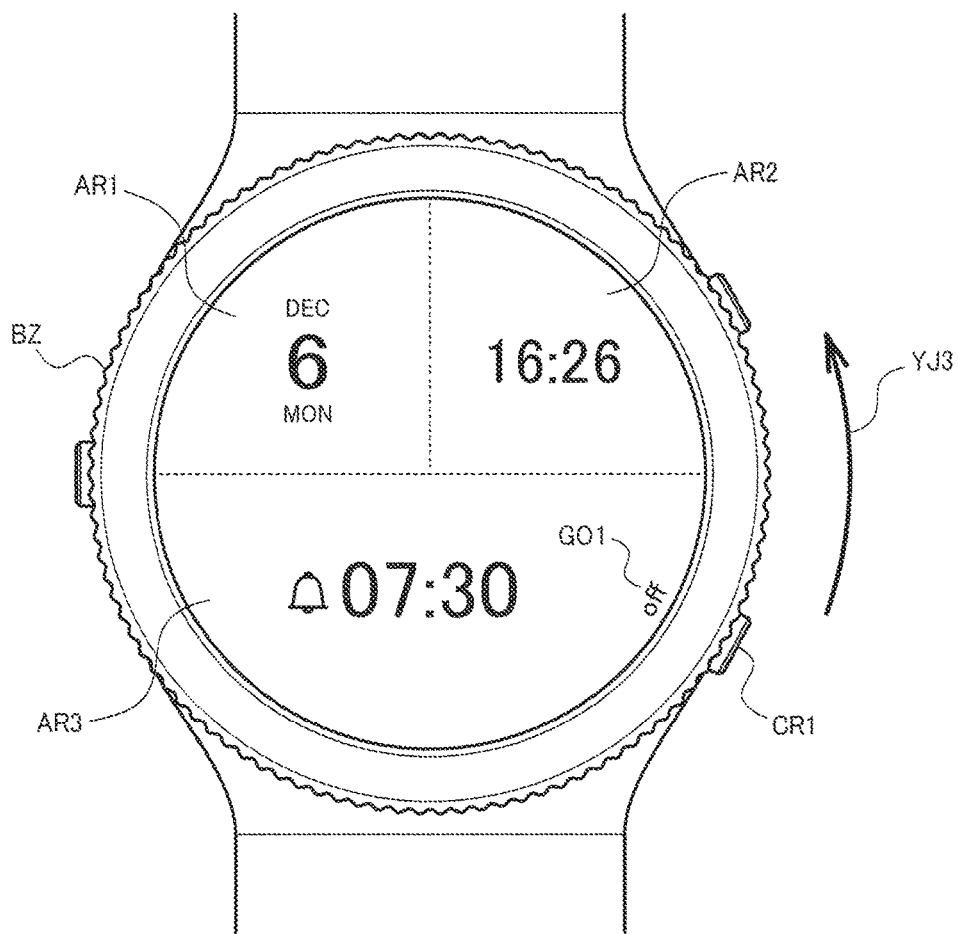
FIG. 7 is an explanatory diagram of anther display image displayed in the daily life mode.

When the display image shown in FIG. 6 is changed to a display image shown in FIG. 7, the display region AR3 is enlarged. In this case, in the display region AR3 shown in FIG. 6, only an icon representing ON/OFF of an alarm is displayed as alarm setting information. In the display region AR3 shown in FIG. 7, set time when the alarm is sounded is also displayed as the alarm setting information in addition to the icon.

In both the examples, more detailed information is displayed in the enlarged display region.

Consequently, it is possible to display, in the enlarged display region, in such a manner as to be easily distinguished and in detail, information that the user desired to know while displaying a plurality of kinds of information in one screen. Since information having a high verbosity is displayed in the enlarged display region, it is unnecessary to reduce a display size of the information to be displayed. It is possible to maintain easiness to distinguish the information.

In this way, the number of objects for transmitting information is larger in the information having the high information verbosity than the information having the low information verbosity. The object (an image object) is a display object displayed in order to transmit information such as a text, a numerical value, or an image.

In other words, the processing section 110 performs processing for displaying R objects (R is any integer) for transmitting information in the i-th display region of the first display image and, when the display image is switched from the first display image to the second display image and the i-th display region is enlarged, displaying objects in number larger than R in the i-th display region of the second display image.

More specifically, for example, the information having the low information verbosity is an icon and the information having the high information verbosity is the icon and numerical value information. That is, the processing section 110 performs processing for displaying, for example, the icon in the i-th display region of the first display image and, when the display image is switched from the first display image to the second display image and the i-th display region is enlarged, displaying, for example, the icon and the numerical value information in the i-th display region of the second display image.

For example, in the example shown in FIGS. 6 and 7, only the icon indicating that the alarm is in an ON state is displayed in the display region AR3 shown in FIG. 6. However, the set time when the alarm is sounded is displayed in addition to the icon in the display region AR3 shown in FIG. 7.

Consequently, when information is displayed in detail, it is possible to, for example, display more objects compared with the normal time and inform the user of a lot of information.

When making it easy for the user to instantaneously grasp information and performing detailed display while reducing the display region by displaying the icon, it is possible to, for example, display accurate and detailed information according to numerical value information.

In this way, concerning information other than information that the user desires to know in detail, it is unnecessary to display a lot of information. It is sufficient that only necessary minimum information can be displayed. Therefore, an information amount to be displayed may be small. A wide display region is unnecessary.

Therefore, when the display image is switched from the first display image to the second display image, the processing section 110 reduces the size of at least the i-th display region. The processing section 110 performs processing for displaying, in the i-th display region of the second display image, information having an information type same as the information type of the information displayed in the i-th display region in the first display image and having an information verbosity lower than and the information verbosity of the information displayed in the i-th display region in the first display image. That is, the processing section 110 performs, in the first display image, processing for displaying the information of the j-th information type in the i-th display region at the first information verbosity and, in the second display image, processing for displaying the information of the j-th information type in the reduced i-th display region at the second information verbosity lower than the first information verbosity.

For example, as explained above, in the first display image shown in FIG. 5, the calendar information for one week is displayed in the display region AR1. However, in the second display image shown in FIG. 6, the calendar information for one day is displayed in the display region AR1, the size of which is reduced. When the display image shown in FIG. 6 is switched to the display image shown in FIG. 7, the display region AR2 is reduced and the time information to be displayed is changed from second units to minute units. In both the examples, information having a low verbosity is displayed in a reduced display region.

Consequently, it is possible to, for example, display, at a necessary minimum information verbosity, information other than information that the user desires to know in detail. A display region where the information other than the information that the user desires to know in detail is reduced. Therefore, it is possible to enlarge a display region where the information that the user desires to know in detail. It is possible to perform efficient information display. Further, since the display region is reduced, even while the user is checking the information that the user desires to know in detail, it is possible to display other information without hindering the user.

As display processing for increasing an information verbosity, the processing section 110 performs at least any one of processing for increasing display items of information concerning the first information, processing for displaying a time series change of the first information, processing for increasing temporal resolution of the time series change of the first information, and processing for displaying derived information derived on the basis of the first information.

Specifically, the processing for increasing the display items of the information concerning the first information is, for example, processing for increasing display items such as numerical value information and explanation information of functions from a state in which the display item is only the icon.

The processing for displaying the time series change of the first information is, for example, processing for displaying, in time series order, the first information acquired within a predetermined period. For example, in that case, the processing section 110 performs processing for displaying a graph, the abscissa of which represents time and the ordinate of which represents a numerical value (a size) or the like that the first information can take. Beside, the processing for displaying the time series change of the first information may be, for example, processing for sliding and displaying the first information in time series order. In that case, after the first information acquired at first timing is displayed, the first information acquired at second timing after the first timing is displayed. This is successively repeated.

Further, the processing for increasing the temporal resolution of the time series change of the first information is, for example, processing for changing the first information displayed in time series in one-day units to be displayed in time series in one-hour units. That is, the processing for increasing the temporal resolution of the time series change is processing for refining (reducing) change units of the time series change. This embodiment is not limited to the change from one-day units to one-hour units. Various modified implementations for, for example, changing the one-hour units to one-minute units or one-second units are possible.

The processing for displaying the derived information derived on the basis of the first information is, for example, processing for additionally displaying information calculated on the basis of the first information. For example, when the first information is a pulse rate, the processing is processing for calculating a difference from an ideal pulse rate as derived information from the pulse rate and additionally displaying the calculated difference from the ideal pulse rate.

Consequently, it is possible to, for example, increase the information verbosity of the first information by increasing display items, displaying a time series change, displaying the time series change more in detail, or displaying information that can be derived from the first information.

When given operation on the operation member 150 is detected by the detecting section 130, the processing section 110 performs processing for switching the display image from the first display image to the second display image and displaying the display image as shown in FIG. 4 or FIGS. 5 to 7.

Consequently, it is possible to, for example, switch the display image from the first display image to the second display image according to the intention of the user.

For example, as explained above, the operation member 150 includes the rotary bezel BZ and the crown shown in FIGS. 5 to 7. In this case, when rotating operation of the operation member 150 is detected as the given operation by the detecting section 130, the processing section 110 performs processing for switching the display image from the first display image to the second display image and displaying the display image. For example, the rotating operation is rotating operation of the rotary bezel BZ or rotating operation of the crown. Besides, the given operation may be, for example, depression of the crown or the button.

Consequently, when the user performs simple operation for rotating the rotary bezel and the crown, it is possible to switch the display image to the first display image to the second display image.

The processing section 110 increases or reduces the size of the i-th display region in a direction corresponding to a rotating direction of the rotating operation.

For example, in the example shown in FIGS. 5 and 6, when the rotary bezel BZ is rotated in the rotating direction indicated by the arrow YJ2 shown in FIG. 6, the detecting section 130 detects rotating operation of the rotary bezel BZ in the direction of the arrow YJ2. When the rotating operation in the direction of YJ2 is detected, the processing section 110 switches the display image from the display image shown in FIG. 5 to the display image shown in FIG. 6 and increases the size of the display region AR2 in a direction corresponding to the direction of YJ2.

On the other hand, when the rotary bezel BZ is rotated in a rotating direction indicated by an arrow YJ1 shown in FIG. 5, the detecting section 130 detects rotating operation of the rotary bezel BZ in the direction of YJ1. When the rotating operation in the direction of YJ1 is detected, the processing section 110 switches the display image from the display image shown in FIG. 6 to the display image shown in FIG. 5 and reduces the size of the display region AR2 in a direction corresponding to the direction of YJ1.

In the example shown in FIGS. 6 and 7, when the rotary bezel BZ is rotated in a rotating direction indicated by an arrow YJ3 shown in FIG. 7, the detecting section 130 detects rotating operation of the rotary bezel BZ in the direction of YJ3. When the rotating operation in the direction of YJ3 is detected, the processing section 110 switches the display image from the display image shown in FIG. 6 to the display image shown in FIG. 7 and increases the size of the display region AR3 in a direction corresponding to the direction of YJ3.

The user determines the rotating direction for rotating the rotary bezel 151 in this way, whereby it is possible to, for example, enlarge any display region. For example, it is possible to, for example, enlarge a display region where information that the user desires to know is displayed. Note that, in the example explained above, the direction in which the display size of the display region is increased or reduced is the same as the rotating direction of the rotating operation. However, this embodiment is not limited to this. For example, the direction in which the display size of the display region is increased or reduced may be opposite to the rotating direction of the rotating operation.

Processing concerning a guide object is explained. When the display image is switched from the first display image to the second display image and the i-th display region is enlarged, the processing section 110 may perform processing for displaying, in a position corresponding to the position of the operation member 150, a guide object for explaining and indicating a command (a function). In that case, when given operation on the operation member 150 is detected by the detecting section 130, the processing section 110 executes a command corresponding to the guide object.

The guide object is indication for indicating to the user that, by performing given operation on an operation member corresponding to the guide object, a command corresponding to the guide object is executed. The command is a command associated with predetermined processing performed by the processing section 110. Specific examples of the command include a command for instructing a start and a stop of a stopwatch and a command for instructing zoom-in display and zoom-out display of a graph.

Figure 8:
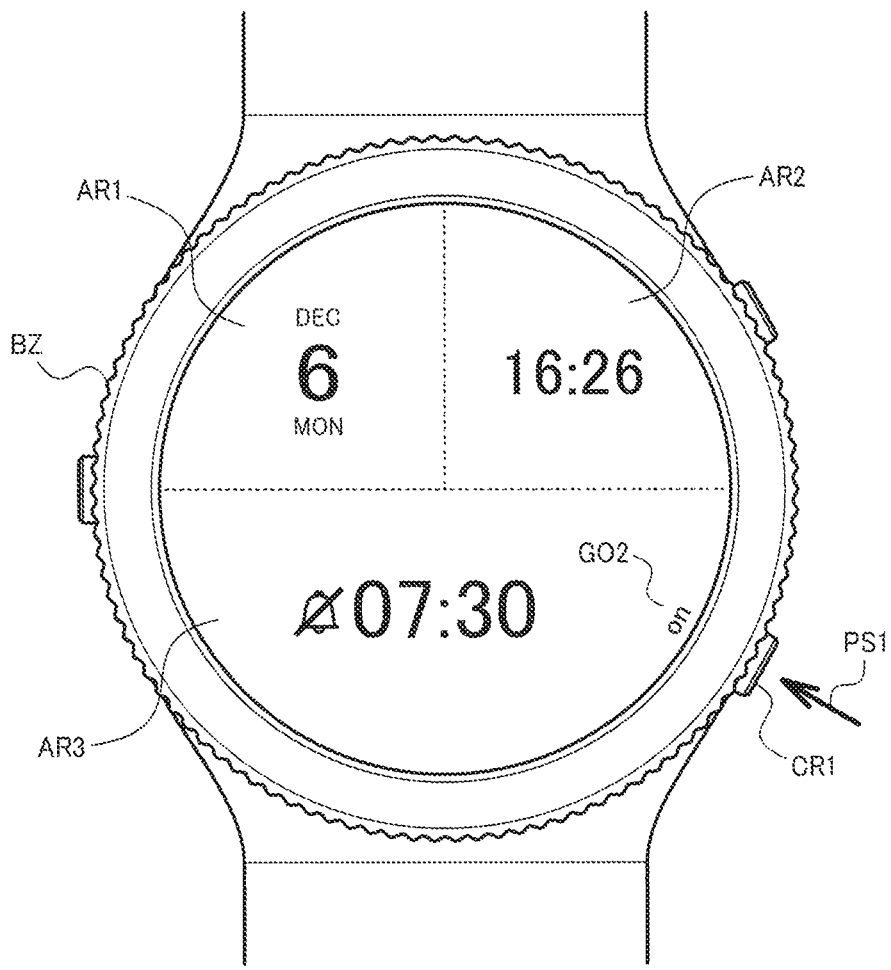
FIG. 8 is an explanatory diagram of a guide object.

A specific example is shown in FIGS. 7 and 8. When the display image shown in FIG. 6 is switched to the display image shown in FIG. 7, the processing section 110 performs processing for displaying a guide object GO1 in the enlarged display region AR3. The guide object GO1 shown in FIG. 7 is guide indication for indicating to the user that, by depressing a crown CR1 present near the guide object GO1, it is possible to change the alarm to an OFF state. The guide object is displayed in a position corresponding to the operation member, for example, near the operation member in the display image. As indicated by an arrow PS1 shown in FIG. 8, when the crown CR1 is depressed, a command for changing the alarm to the OFF state is executed, the alarm is changed to the OFF state, and the icon is changed to an icon indicating the OFF state. At the same time, the guide object is changed to a guide object GO2 indicating that the alarm is changed to the ON state.

Consequently, it is possible to, for example, smoothly guide operation by the user to a function corresponding to information displayed in the enlarged display region. That is, by displaying the guide object, it is possible to, for example, make it easy for the user to grasp which operation member 150 the user should operate to be able to operate the function of the wearable terminal device.

A specific example of information types is shown in FIG. 9. The information types are roughly classified into, for example, biological detection information, activity detection information, date and time information, environment detection information, and other application information.

The biological detection information is, for example, information concerning an organism of the wearer (the user) of the wearable terminal device 100. The biological detection information is, for example, sensor detection information measured by a pulse wave sensor or the like provided in the wearable terminal device 100 and information input by the user. Specifically, examples of the biological detection information include information concerning a pulse rate (a pulse wave, a pulse) and blood pressure.

The activity detection information is, for example, information concerning an activity result of the wearer (the user) of the wearable terminal device 100. The activity detection information is, for example, sensor detection information measured by an acceleration sensor and the like provided in the wearable terminal device 100 and information input by the user. Specifically, examples of the activity detection information include information concerning the number of steps and a moving distance.

The date and time information is information representing time of day (time) and a date. Specifically, examples of the date and time information include information concerning a date (a calendar), time of day (a watch), and alarm setting.

The environment detection information is, for example, information concerning an environment around the wearable terminal device 100. Specifically, examples of the environment detection information include information concerning temperature, humidity, altitude, atmospheric pressure, and an azimuth (a direction). These kinds of information are respectively acquired by a temperature sensor, a humidity sensor, an atmospheric pressure sensor, an azimuth sensor, and the like provided in the wearable terminal device 100. The environment detection information may be, for example, information acquirable from an electronic apparatus (e.g., a server) connected to the wearable terminal device 100 via a network.

The other application information is information concerning functions of the wearable terminal device 100 and an electronic apparatus and the like communicatively connected to the wearable terminal device 100. Examples of the other application example include information concerning a stopwatch and a music player. Note that the information types in this embodiment are not limited to the example shown in FIG. 9 and can include other information types.

The information of the first information type to the information of the Nth information type displayed on the display image include at least one of the biological detection information and the activity detection information and at least one of the time information and the environment detection information.

Consequently, it is possible to, for example, simultaneously display at least two kinds of information on the display section 120.

In other words, the information displayed on the display section 120 is information concerning any one of a pulse rate, the number of steps, an azimuth, time of day, date and time, an activity amount, a calorie balance, and a sleeping time.

Consequently, it is possible to, for example, display, in any display region, the information concerning any one of the pulse rate, the number of steps, the azimuth, the time of day, the date and time, the activity amount, the calorie balance, and the sleeping time while changing the information verbosity as appropriate.

The wearable terminal device 100 in this embodiment is capable of switching a daily life mode and an exercise mode and switching the display image in the respective modes.

Specifically, the processing section 110 performs switching processing of the daily life mode and the exercise mode and, when the wearable terminal device 100 is set in the daily life mode, displays P kinds of information (P is an integer equal to or larger than 1 and equal to or smaller than N) of an information type associated with the daily life mode among the information of the first information type to the information of the N-th information type.

When the wearable terminal device 100 is set in the exercise mode, the processing section 110 performs processing for displaying Q pieces of information (Q is an integer equal to or larger than 1 and equal to or smaller than N) of an information type associated with the exercise mode among the information of the first information type to the information of the N-th information type.

For example, the respective information types are associated with the respective modes as shown in FIG. 9. Specifically, for example, date and time information such as a date (a calendar), time of day (a watch), and alarm setting and a music player are associated with the daily life mode. For example, biological detection information such as a pulse rate and blood pressure, activity detection information such as the number of steps and a moving distance, environment detection information such acrownperature, humidity, altitude, atmospheric pressure, and an azimuth, a stopwatch, and a music player are associated with the exercise mode. Note that an information type associated with both the modes like the music player may be present.

FIGS. 5 to 8 are the examples of the daily life mode. Examples of the exercise mode are shown in FIGS. 10 to 16. In the examples shown in FIGS. 10 to 16, a display image is divided into five display regions (AR1 to AR5). Information concerning a pulse rate is displayed in the first display region AR1. Information concerning altitude is displayed in the second display region AR2. Information concerning a stopwatch is displayed in the third display region AR3. Information concerning the number of steps is displayed in the fourth display region AR4. Information concerning an azimuth is displayed in the fifth display region AR5.

Consequently, it is possible to, for example, display, in the daily life mode, information that the user frequently view in a daily life and display, in the exercise mode, information that the user views during exercise. Note that, as in the examples shown in FIGS. 5 to 8 and FIGS. 10 to 16, the number of display regions in the display image may be different or may be the same in the daily life mode and the exercise mode. Information types displayed in both the modes may be present.

Figure 10:
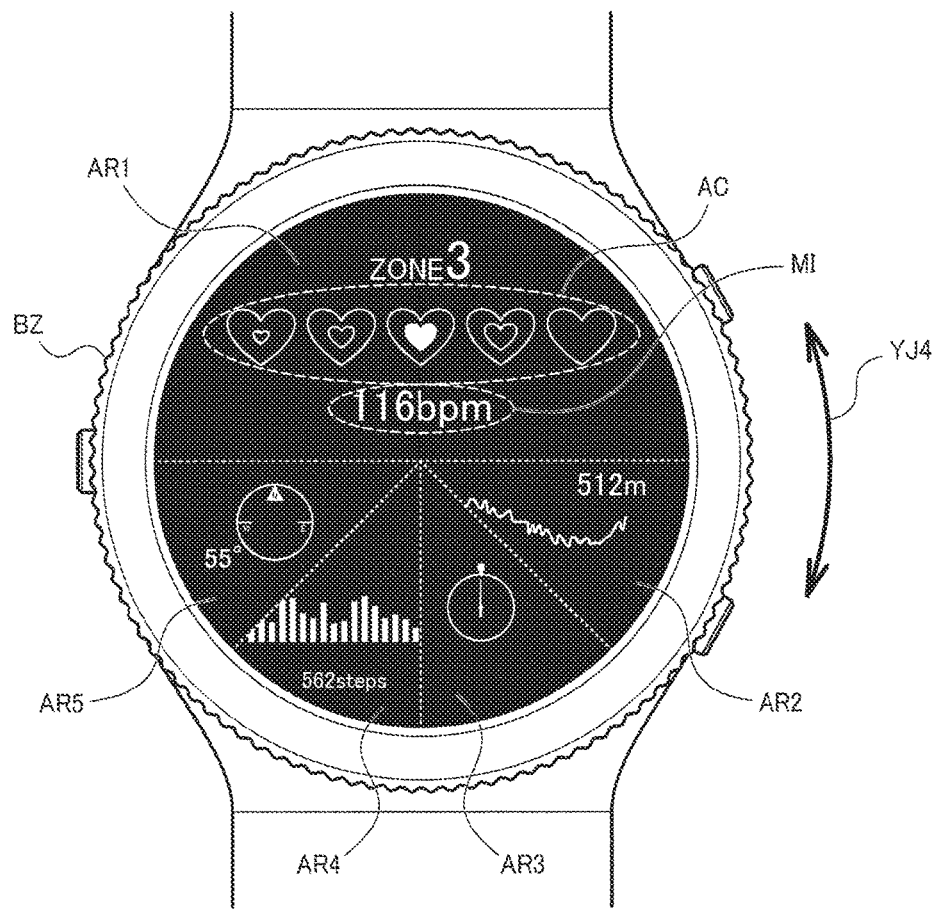
FIG. 10 is an explanatory diagram of a display image displayed in an exercise mode.

The examples shown in FIGS. 10 to 16 are specifically explained. In FIG. 10, the display region AR1 is enlarged. In the display region AR1, detailed information concerning a pulse rate is displayed. For example, in the example shown in FIG. 10, an icon AC representing a level of a pulse rate in zones (levels) of five stages and numerical value information MI of an actually measured pulse rate are displayed. As indicated by an arrow YJ4, it is possible to switch the display image by rotating the rotary bezel BZ. Note that the information concerning the pulse rate may include, besides the above, for example, a minimum pulse rate, a resting pulse rate, an average pulse rate, a maximum pulse rate, and a graph indicating a time series change of the pulse rate. The user may be able to select information displayed as information with a high information verbosity concerning the pulse rate and information displayed as information with a low information verbosity concerning the pulse rate. The pulse rate may be set as a specified value. For example, the user may be able to select to display, as the information with the high information verbosity, for example, the minimum pulse rate, the resting pulse rate, the average pulse rate, the maximum pulse rate, and the graph indicating the time series change of the pulse rate and display the icon or the like as the information with the low information verbosity.

Figure 11:
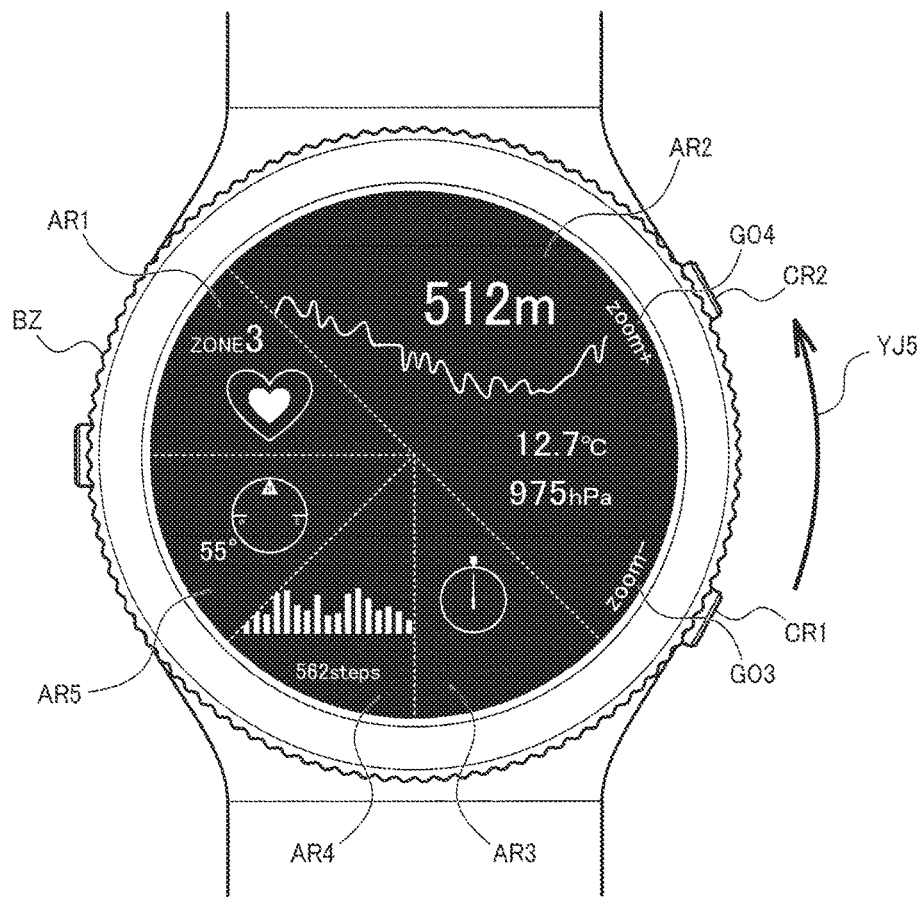
FIG. 11 is another explanatory diagram of the display image displayed in the exercise mode.

For example, when the rotary bezel BZ is rotated in a direction indicated by an arrow YJ5 shown in FIG. 11, a display image shown in FIG. 10 is switched to a display image shown in FIG. 11. At this point, in the display image shown in FIG. 11, the display region AR2 is enlarged. In the display region AR2, detailed information concerning altitude is displayed. For example, in the display region AR2 shown in FIG. 11, in addition to specific numerical value information (512 m) representing altitude, a line graph representing a history of altitude at moving points in the past, temperature (12.7°), and atmospheric pressure (975 hPa) are also displayed.

Figure 12:
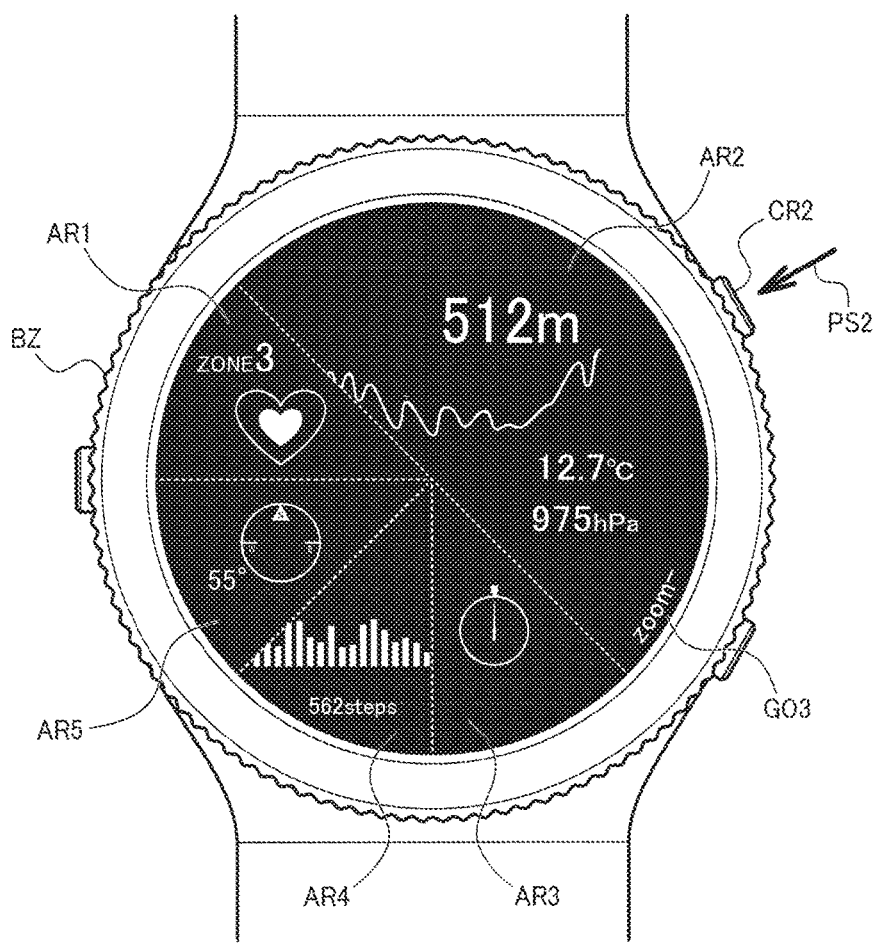
FIG. 12 is an explanatory diagram of a function for zooming-in a graph representing a history of altitude.

Further, in the display region AR2 shown in FIG. 11, a guide object GO3 and a guide object GO4 are also displayed. The guide object GO3 indicates that a graph of a history of altitude can be zoomed out and displayed when the crown CR1 corresponding to the guide object GO3 is operated. The guide object GO4 indicates that the graph of the history of altitude can be zoomed in and displayed when a crown CR2 corresponding to the guide object GO4 is operated. For example, as shown in FIG. 12, when the crown CR2 is depressed as indicated by an arrow PS2, the processing section 110 executes a command for displaying, as a graph, only a most recent history concerning altitude. When the graph is zoomed in to the maximum, the processing section 110 performs processing for hiding the guide object GO4 as shown in FIG. 12.

Subsequently, when the rotary bezel BZ is rotated in a direction indicated by an arrow YJ6 shown in FIG. 13, the display image shown in FIG. 11 (or FIG. 12) is switched to a display image shown in FIG. 13. At this point, in the display image shown in FIG. 13, the display region AR3 is enlarged. In the display region AR3, detailed information concerning a stopwatch is displayed. For example, in the display region AR3 shown in FIG. 13, the present measurement time and a guide object GO5 are displayed. The guide object GO5 indicates that the stopwatch can be started when the crown CR2 corresponding to the guide object OG5 is operated.

Figure 13:
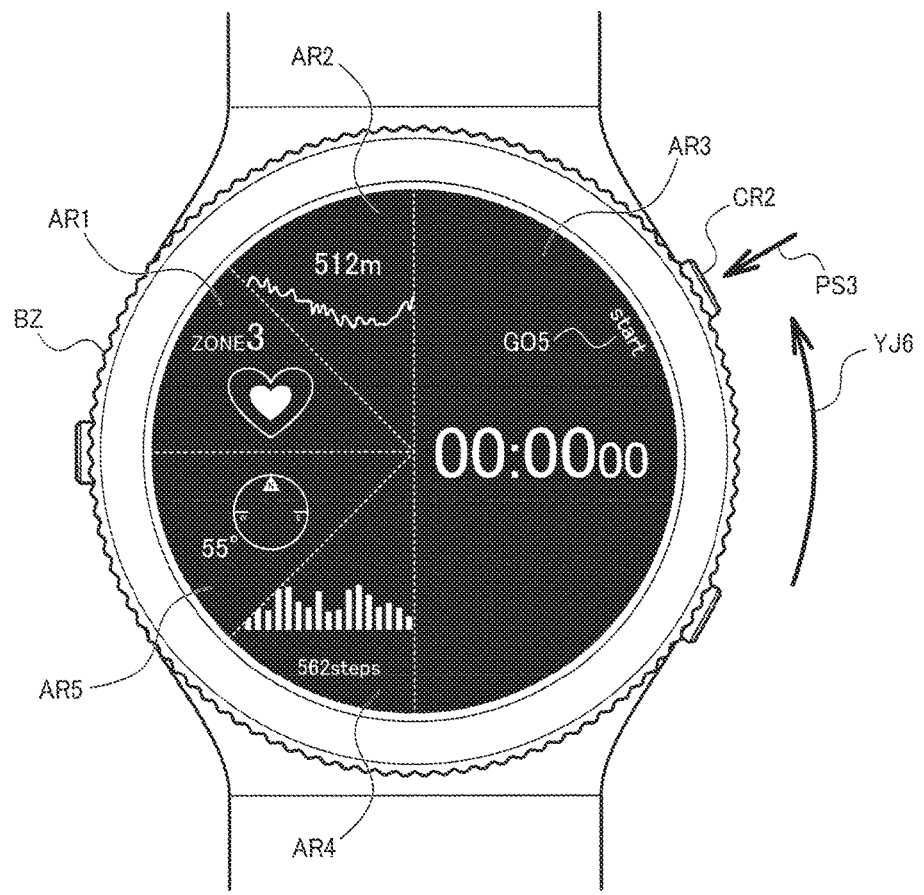
FIG. 13 is an explanatory diagram of another display image displayed in the exercise mode.
Figure 14:
FIG. 14 is an explanatory diagram of a stopwatch function.

When the crown CR2 is depressed to start measurement as indicated by an arrow PS3 shown in FIG. 13, as shown in FIG. 14, a guide object GO6 and a guide object GO7 are displayed anew. The guide object GO6 indicates that a lap time can be acquired when the crown CR1 corresponding to the guide object GO6 is operated. The guide object GO7 indicates that the measurement can be stopped when the crown CR2 corresponding to the guide object GO7 is operated.

Figure 15:
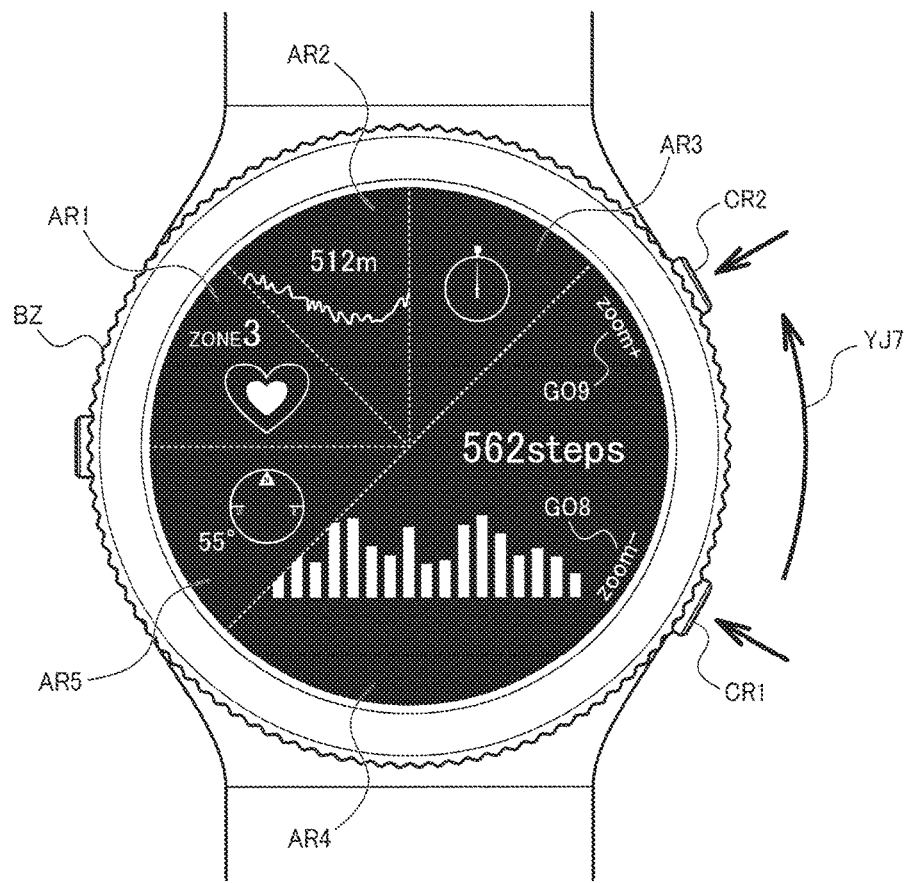
FIG. 15 is an explanatory diagram of another display image displayed in the exercise mode.

Further, when the rotary bezel BZ is rotated in a direction indicated by an arrow YJ7 shown in FIG. 15, the display image shown in FIG. 13 (or FIG. 14) is switched to a display image shown in FIG. 15. At this point, in the display image shown in FIG. 15, the display region AR4 is enlarged. In the display region AR4, detailed information concerning the number of steps is displayed. For example, in the display region AR4 shown in FIG. 15, the present cumulative number of steps (of the day) (562 steps), a bar graph of a cumulative number of steps of each day, and two guide objects (GO8 and GO9) are displayed. Like the guide objects (GO3 and GO4) explained above with reference to FIG. 11, the two guide objects (GO8 and GO9) indicate zoom-in and zoom-out of a graph. Therefore, detailed explanation of the guide objects (GO8 and GO9) is omitted. Note that the information concerning the number steps may include, besides the above, a progress degree with respect to a target number of steps, a cumulative number of steps of each time, and a maximum of daily cumulative numbers of steps measured in the past. The user may be able to select information displayed as information with a high information verbosity concerning the number of steps and information displayed as information with a low information verbosity concerning the number of steps. The number of steps may be set as a specified value. For example, the user may be able to select to display, as the information with the high information verbosity, for example, the bar graph of the cumulative number of steps of each day and display, as the information with the low information verbosity, for example, the progress degree with respect to the target number of steps.

Figure 16:
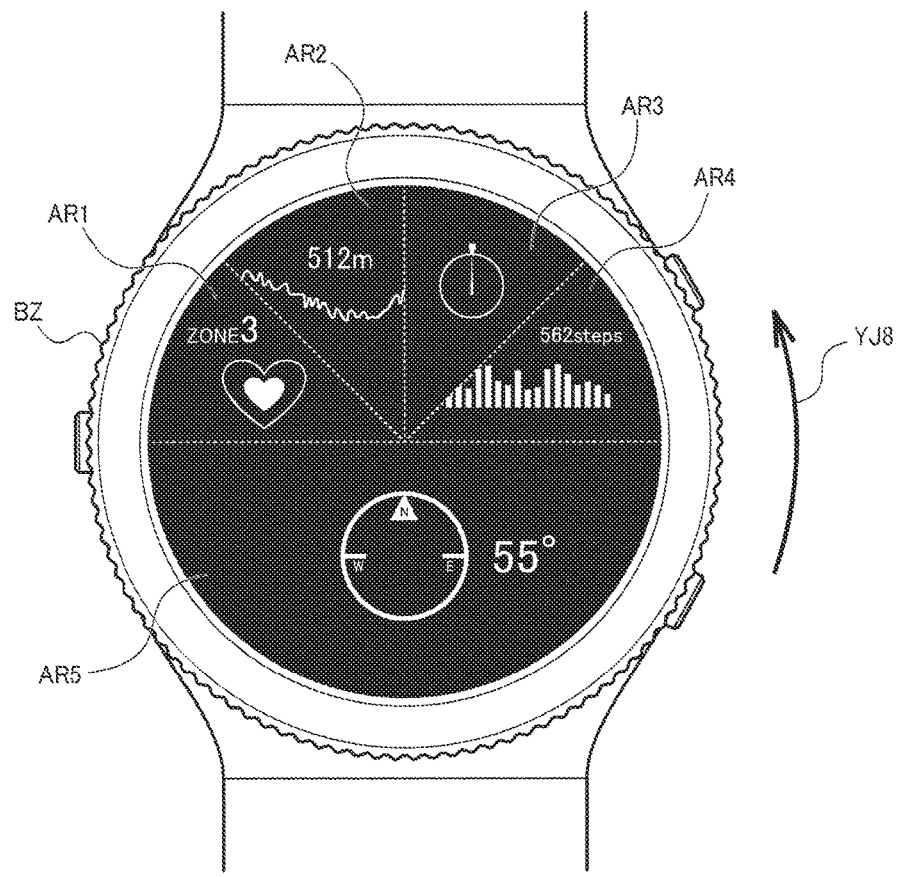
FIG. 16 is an explanatory diagram of another display image displayed in the exercise mode.

Further, when the rotary bezel BZ is rotated in a direction indicated by an arrow YJ8 shown in FIG. 16, the display image shown in FIG. 15 is switched to a display image shown in FIG. 16. At this point, in the display image shown in FIG. 16, the display region AR5 is enlarged. In the display region AR5, detailed information concerning an azimuth is displayed. For example, in the display region AR5 shown in FIG. 16, a specific numerical value (55°) representing a difference between an image indicating an azimuth that the user (or the wearable terminal device 100) currently faces and a given direction is displayed. Note that the information concerning the azimuth may include, besides the above, a time series change of an azimuth angle, an object representing an azimuth indicating a direction of a destination, and an angle of deviation, which is a difference between a magnetic north in the present location and the true north (north on a map). The user may be able to select information displayed as information with a high information verbosity concerning an azimuth and information displayed as information with a low information verbosity. For example, the user may be able to display, as the information with the high information verbosity, for example, a time series change of an azimuth angle and display, as the information with the low information verbosity, for example, an icon of the azimuth that the user (or the wearable terminal device 100) currently faces.

In the above explanation, the display image includes the display regions divided into the pie shapes. However, this embodiment is not limited to this. That is, the display regions of the first display region to the M-th display region of the display image may be divided into the pie shapes or may be formed in concentric circle shapes.

Figure 17:
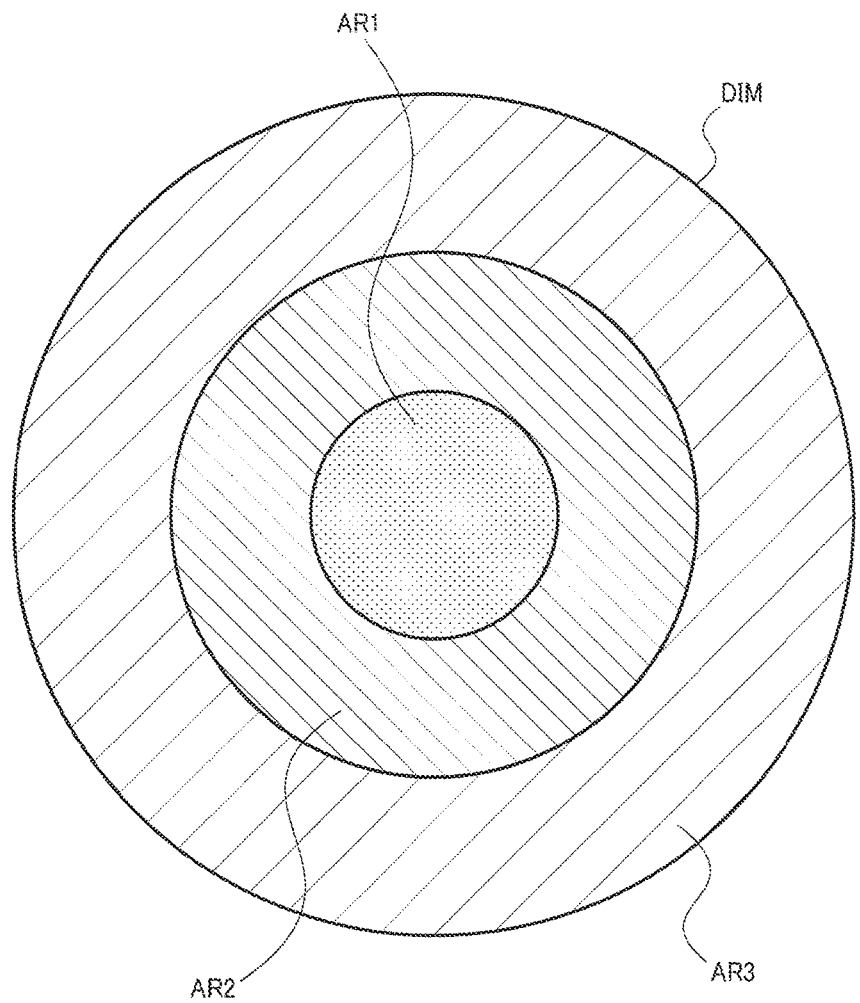
FIG. 17 is another explanatory diagram of a display image and a plurality of display regions.

For example, an example of a display image in which display regions are formed in concentric circle shapes is shown in FIG. 17. The display image DIM shown in FIG. 17 includes the first display region AR1, the second display region AR2, and the third display region AR3. The first display region AR1, the second display region AR2, and the third display region AR3 are disposed from the inner side to the outer side of the display image in this order. In this case, the first display region AR1 is a circular display region. The second display region AR2 is a belt-like display region surrounding the first display region AR3. The third display region AR3 is a belt-like display region surrounding the second display region AR2.

Consequently, it is possible to, for example, efficiently make use of a display space and display information that is more clearly understood when being disposed in a circular shape.

When the display image includes the display regions divided into the pie shapes, the sizes of the display regions do not have to be uniform. A part of the display regions may overlap a part of other display regions.

In the above explanation, when the rotary bezel is rotated, the divisions of the display regions changes and the display region and the information displayed in the display region move together in the display image. However, this embodiment is not limited to this. For example, a modified implementation is also possible in which, as shown in an example shown in FIG. 18, when divisions (sizes and shapes) of the display regions are fixed and the rotary bezel is rotated, only the information displayed in the display regions is seen as if gradually shifting at a glance.

Figure 18:
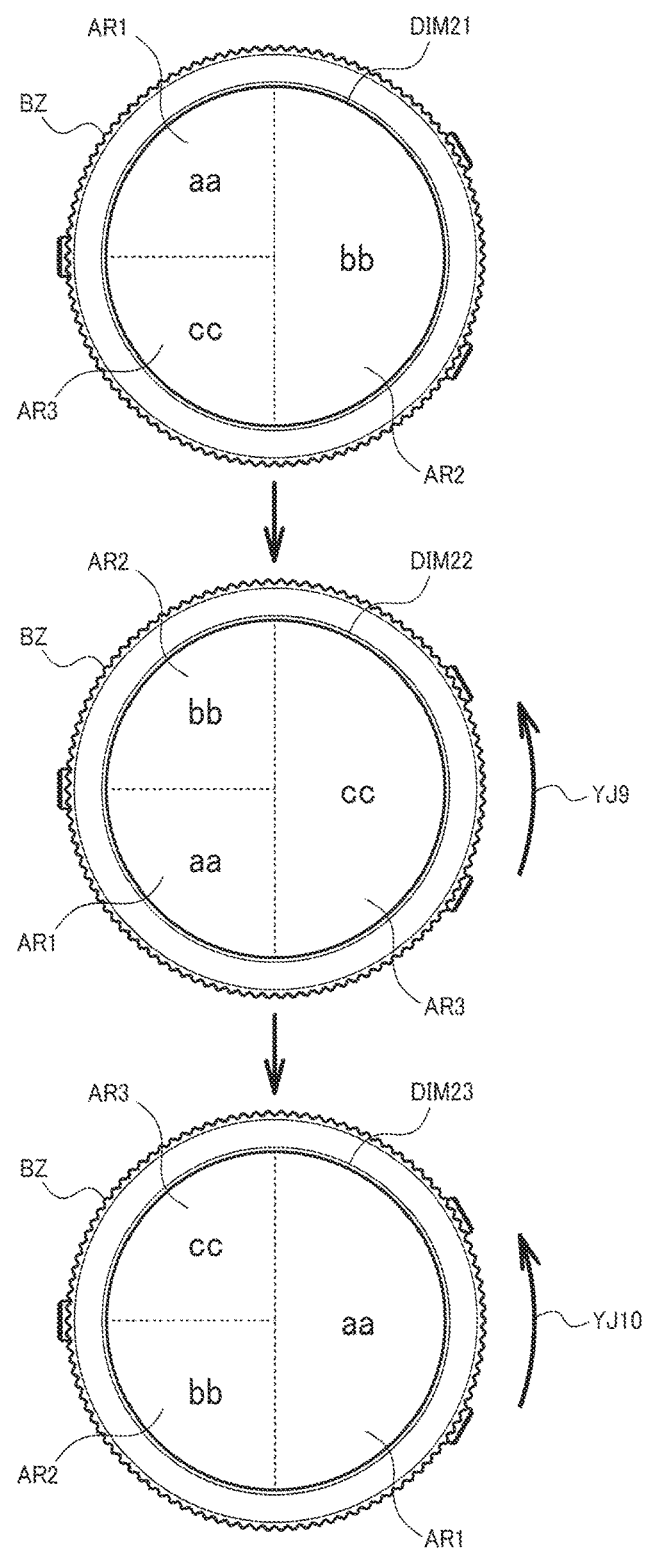
FIG. 18 is an explanatory diagram of a special example of switching processing for a display image.

For example, in the example shown in FIG. 18, the display image includes three display regions (AR1 to AR3). In a first display image DIM21, information aa is displayed in the display region AR, information bb is displayed in the display region AR2, and information cc is displayed in the display region AR3.

In this case, when the rotary bezel BZ is rotated as indicated by an arrow YJ9 shown in FIG. 18, the display image is switched from the display image DIM21 to a display image DIM22. The processing section 110 displays the display image as if only the information displayed in the display regions is shifted in a direction corresponding to a rotating direction at a glance without changing divisions of the three display regions (AR1 to AR3). Actually, in the display image DIM22, the display region AR1 moves to the position of the display region AR3 in the display image DIM21 and changes to a shape same as the shape of the original display region AR3. Similarly, in the display image DIM22, the display region AR2 moves to the position of the display region AR1 in the display image DIM21 and changes to a shape same as the shape of the original display region AR1. The display region AR3 moves to the position of the display region AR2 in the display image DIM21 and changes to a shape same as the shape of the original display region AR2. The processing section 110 changes the information verbosities according to the sizes of the display regions without changing the information types of the information displayed in the display regions.

Similarly, when the rotary bezel BZ is rotated as indicated by an arrow YJ10 shown in FIG. 18, the processing section 110 displays the display image as if only the information displayed in the display regions is shifted in a direction corresponding to a rotating direction at a glance without changing divisions of the three display regions (AR1 to AR3).

The example shown in FIG. 18 is a special example of the example explained above with reference to FIG. 4 and the like. In the example shown in FIG. 18, the display image includes a plurality of display regions. An i-th display region and a k-th display region are adjacent to each other. When the display image is switched from the first display image to the second display image, the i-th display region in the second display image is moved to a position same as the position of the k-th display region in the first image and changed to a shape same as the shape of the k-th display region. The same applies to the other display regions. As a result, divisions of the display regions are seen not changed at a glance. In this way, in the example shown in FIG. 18, the divisions of the display regions in appearance do not change. However, when grasped as explained above, the example is essentially the same as the example in which the divisions of the display regions change as shown in FIG. 4. In the example shown in FIG. 18, when the display image is switched from the first display image to the second display image, in the first display image, the information of the j-th information type is displayed in the i-th display region at the first information verbosity. In the second display image, the information of the j-th information type is displayed in the i-th display region, the size of which is changed, at the second information verbosity different from the first information verbosity. Therefore, the example shown in FIG. 18 is also considered a modification of this embodiment.

This embodiment is explained in detail above. However, those skilled in the art can easily understand that many modifications are possible without substantially departing from the new matters and the effects of the invention. Therefore, all such modifications are included in the scope of the invention. For example, terms described together with broader-sense or synonymous different terms at least once in the specification or the drawings can be replaced with the different terms in any part of the specification or the drawings. The configurations and the operations of the wearable terminal device and the like are not limited to the configurations and the operations explained in this embodiment. Various modified implementations are possible.

What is claimed is:

1. A wearable terminal device comprising:
   a display section configured to display an image; and
   at least one processor configured to perform display control of the image displayed by the display section,
   wherein the at least one processor performs processing for
      displaying any one kind of information among information of a first information type to information of an N-th information type (N is an integer equal to or larger than 2) in each of a plurality of display regions including a first display region to an M-th display region (M is an integer equal to or larger than 2),
      changing, when the image is switched from a first image to a second image, a size of an i-th display region (i is an integer equal to or larger than 1 and equal to or smaller than M) among the plurality of display regions from a first size to be displayed at a second size different from the first size and changing a size of an M-th display region among the plurality of display regions from the second size to be displayed at the first size, and
      changing, when the image is switched from the first image to the second image, an information verbosity of information of a j-th information type (j is an integer equal to or larger than 1 and equal to or smaller than N) displayed in the i-th display region from a first information verbosity to a second information verbosity different from the first information verbosity and changing an information verbosity of an N-th information type displayed in the M-th display region from the second information verbosity to the first information verbosity.

2. The wearable terminal device according to claim 1, wherein, when the image is switched from the first image to the second image, the at least one processor
   increases the size of the i-th display region and increases the information verbosity of the information of the j-th information type in the enlarged i-th display region to the second information verbosity, which second information verbosity is higher than the first information verbosity, and
   reduces the size of the M-th display region and decreases the information verbosity of the information of the N-th information type in the reduced M-th display region to the first information verbosity, which first information verbosity is lower than the second information verbosity.

3. The wearable terminal device according to claim 1, wherein, when the image is switched from the first image to the second image, the at least one processor
   reduces the size of the i-th display region and reduces the information verbosity of the information of the j-th information type in the reduced i-th display region to the second information verbosity, which second information verbosity is lower than the first information verbosity, and
   increases the size of the M-th display region and increases the information verbosity of the information of the N-th information type in the enlarged M-th display region to the first information verbosity, which first information verbosity is higher than the second information verbosity.

4. The wearable terminal device according to claim 1, wherein the information of the first information type to the information of the N-th information type include at least one of biological detection information and activity detection information and at least one of time information and environment detection information.

5. The wearable terminal device according to claim 1, further comprising a sensor configured to detect operation of an operation member,
   wherein the at least one processor performs processing for, when a first given operation on the operation member is detected by the sensor, switching the image from the first image to the second image and displaying the image.

6. The wearable terminal device according to claim 5, wherein
   the operation member is a member rotatable around a given rotation axis, and
   the at least one processor performs processing for, when a rotating operation of the operation member serving as the given operation is detected by the sensor, switching the image from the first image to the second image and displaying the image.

7. The wearable terminal device according to claim 6, wherein the at least one processor increases or reduces the size of the i-th display region and the M-th display region in a direction corresponding to a rotating direction of the rotating operation.

8. The wearable terminal device according to claim 5, wherein the at least one processor performs processing for
   when the image is switched from the first image to the second image and the i-th display region is enlarged, displaying a guide object of a command in a position corresponding to a position of the operation member and,
   when a second given operation on the operation member is detected by the sensor, executing the command corresponding to the guide object.

9. The wearable terminal device according to claim 1, wherein the at least one processor performs switching processing of a daily life mode and an exercise mode and performs processing for, when the wearable terminal device is set in the daily life mode, displaying P kinds of information (P is an integer equal to or larger than 1 and equal to or smaller than N) of an information type associated with the daily life mode among the information of the first information type to the information of the N-th information type and, when the wearable terminal device is set in the exercise mode, displaying Q pieces of information (Q is an integer equal to or larger than 1 and equal to or smaller than N) of an information type associated with the exercise mode among the information of the first information type to the information of the N-th information type.

10. The wearable terminal device according to claim 1, wherein a number of objects for transmitting information is larger for information, the information verbosity of which is high, than information, the information verbosity of which is low.

11. The wearable terminal device according to claim 1, wherein
information, the information verbosity of which is low, is an icon, and
information, the information verbosity of which is high, is the icon and numerical value information.

12. The wearable terminal device according to claim 1, wherein the display regions of the first display region to the M-th display region are divided into pie shapes or are formed in concentric circle shapes.

13. The wearable terminal device according to claim 1, wherein the at least one processor is configured to perform processing of displaying biological detection information or activity detection information in a first display region among the first display region to an M-th display region (M is an integer equal to or larger than 2) obtained by dividing the image into pie shapes or concentric circle shapes and displaying time information or environment detection information in a second display region among the first display region to the M-th display region.

14. A wearable terminal device comprising:
a display section including a first display region for displaying first information and a second display region for displaying second information;
at least one processor configured to perform display control of the display section; and
an operation member that is in an electric communication relation with the at least one processor,
wherein the at least one processor performs, on the basis of a signal from the operation member, processing for changing the first display region from a first size to a second size that is larger than the first size,
changing the second display region from the second size to the first size,
increasing an information verbosity concerning the first information displayed in the first display region from a first information verbosity to a second information verbosity, and
decreasing an information verbosity concerning the second information displayed in the second display region from the second information verbosity to the first information verbosity.

15. The wearable terminal device according to claim 14, wherein the at least one processor performs, as the display processing for increasing the information verbosity, at least any one kind of processing among processing for increasing display items of information concerning the first information, processing for displaying a time series change of the first information, processing for increasing temporal resolution of the time series change of the first information, and processing for displaying derived information derived on the basis of the first information.

16. The wearable terminal device according to claim 14, wherein the first information is information concerning any one of a pulse rate, a number of steps, an azimuth, time of day, date and time, an activity amount, a calorie balance, and a sleeping time.

17. An image processing method comprising:
performing processing for displaying any one kind of information among information of a first information type to information of an N-th information type (N is an integer equal to or larger than 2) in each of a plurality of display regions including a first display region to an M-th display region (M is an integer equal to or larger than 2);
increasing, when a displayed image is switched from a first image to a second image, a size of an i-th display region (i is an integer equal to or larger than 1 and equal to or smaller than M) among the plurality of display regions from a first size to be displayed at a second size different from the first size and decreasing a size of an M-th display region among the plurality of display regions from the second size to be displayed at the first size; and
when the displayed image is switched from the first image to the second image, changing an information verbosity of information of a j-th information type (j is an integer equal to or larger than 1 and equal to or smaller than N) displayed in the i-th display region from a first information verbosity to a second information verbosity different from the first information verbosity and changing an information verbosity of an N-th information type displayed in the M-th display region from the second information verbosity to the first information verbosity.

* * * * *